United States Patent [19]
Spencer et al.

[11] Patent Number: 5,776,133
[45] Date of Patent: Jul. 7, 1998

[54] BONE SETTING APPARATUS

[76] Inventors: Edward Spencer, 3260 E. 9425 South, Sandy, Utah 84092; Randy Telford, 1804 E. Carriage Park Cir., Salt Lake City, Utah 84121

[21] Appl. No.: 718,211

[22] Filed: Sep. 20, 1996

[51] Int. Cl.⁶ ............................................. A61B 17/60
[52] U.S. Cl. ........................... 606/57; 606/53; 606/54; 606/105
[58] Field of Search ........................ 606/53, 54, 57, 606/105

[56] References Cited

U.S. PATENT DOCUMENTS

| | | |
|---|---|---|
| 2,112,447 | 3/1938 | Peterson . |
| 2,371,519 | 3/1945 | Haynes ................................. 606/54 |
| 3,709,219 | 1/1973 | Halloran . |
| 4,365,624 | 12/1982 | Jaquet . |
| 4,823,781 | 4/1989 | Buchanan . |
| 4,929,247 | 5/1990 | Rayhack . |
| 5,100,403 | 3/1992 | Hotchkiss et al. . |
| 5,397,322 | 3/1995 | Campopiano . |
| 5,437,668 | 8/1995 | Aronson et al. . |
| 5,443,464 | 8/1995 | Russell et al. . |

FOREIGN PATENT DOCUMENTS

| | | | |
|---|---|---|---|
| 1080370 | 12/1954 | France | ................................. 606/105 |
| 36 14 305.7 | 4/1986 | Germany . | |

*Primary Examiner*—Michael Buiz
*Assistant Examiner*—Daphna Shai
*Attorney, Agent, or Firm*—Thorpe, North & Western, L.L.P.

[57] ABSTRACT

A bone setting apparatus is disclosed including an elongate shaft with a distal working arm and an intermediate working arm attached thereto so as to extend generally perpendicular to the shaft. The working arms are of sufficient length and thickness to act as leveraging bars to reduce a compound fracture. Preferably, the working arms have a concave contact surface for engaging the limb on which the apparatus will be used. Disposed at an end of the shaft opposite the distal and intermediate working arms is a torque control mechanism which extends outwardly from the shaft and can be used to accurately control rotation of the shaft as it is pivoted in such a manner that the distal and intermediate arms align fractured portions of a bone.

21 Claims, 3 Drawing Sheets

BONE SETTING APPARATUS

BACKGROUND OF THE INVENTION

1. Field of the Invention

The present invention relates to a bone setting apparatus, and more particularly to an apparatus which may be used to reduce bones which have suffered a compound fracture in order to properly position the bone for setting, thereby facilitating proper healing of the fracture.

2. State of the Art

Compound fractures are a relatively common occurrence in society today. In a compound fracture the bone undergoes sufficient trauma that it literally breaks in half. In order to properly heal, the bone must be placed back into alignment and held in place for a sufficient length of time for the piece of bone to be fused together via new bone growth. In order to hold the two pieces of bone in the correct position, a retention device is used. The retention device can be a plate which is attached by screws or some similar mechanism on the outside of the bone. In the alternative, a retention pin which is disposed in the cavity extending through the center of the bone may also be used.

Regardless of which approach is used, the two pieces of bone must be properly aligned or "reduced" for the bone to heal properly. While realignment of the bone is often not difficult with small bones, such as those present in hands and feet, it can present a major problem for large bones such as the femur. When the bone fractures into two or more pieces, the muscles surrounding the bone tends to constrict and draw the opposing ends of the bone together, forcing the portions adjacent the fracture out of alignment with one another. Where a bone is surrounded by large amounts of muscle tissue, such as the leg, considerable force may be necessary to overcome the contractions of the muscles and realign the pieces of the bone.

Numerous approaches have been tried to facilitate proper placement of the bones. For example, in U.S. Pat. No. 2,112,447 there is disclosed a device which can be used for the setting of bones, and the refracture of bones which have set improperly. The device included an elongate lever which had a pair of jaw members extending outwardly therefrom in a parallel orientation.

The device shown in the '447 patent was designed for setting medium sized bones, such as those in the arm. To facilitate setting, the device was positioned so that one of the jaw members was positioned above one portion of the bone that needed to be moved downward, and the other jaw member was disposed below the portion of the bone which needed to be lifted to properly set the bone. The lever was then rotated about an axis perpendicular to the long axis of the lever. Typically, the point of rotation was aligned so that the axis about which the lever was rotated aligned with the fracture. By applying force to the lever, the two misaligned portions of the bone were brought into the same plane.

Unfortunately, the device suffers from a flaw which has rendered the device unusable for placement of large bones. Specifically, applying a considerable amount of force to the handle creates a significant amount of torque. When used on a slick surface, such as skin having blood or oil disposed thereon, the elongate jaw members can easily slide from their original position causing considerable turning motion. The force of the turning motion or torque easily may be sufficient to cause the jaw members to slip off the limb of the patient. Occasionally, the torque may be sufficient that the operator looses his or her grip on the elongate lever. Due to the significant amount of pressure that is applied to the lever in order to set the bones, the device can become a hazard if it slips off a patient's limb.

There are also situations in which it is desirable for the physician to be able to manipulate the instrument to cause torque on the bone in order to move the bone into the desired location. However, with the prior art device it is extremely difficult to control torque sufficiently to manipulate the bone in the desired direction. Essentially, the wrist of the user must provide virtually all of the force and control. At the levels of force often required, however, most users do not have sufficient strength to achieve the desired amount of control.

While it has long been desired to facilitate the quick and accurate placement of compound fractures, particularly in the bones of the leg, designs such as that shown in U.S. Pat. No. 2,112,447 have not been widely used. Rather, most modern approaches have used a plurality of pins which are inserted into the pieces of bone and connected to a movable frame. Once the pins have been worked into each portion of the bone, the frame is adjusted to relocate the pins relative to each other until the ends of the two pieces of bone are in a proper alignment. Examples of such devices are shown in U.S. Pat. Nos. 3,709,219; 4,365,624; 4,823,781; 4,929,247; 5,397,322; 5,437,668; and 5,443,464.

While such devices are currently in common use, they have the distinct disadvantage that they require extensive invasion into the limb of the patient. Not only must some plate or pin be attached to the bone to hold it in place, numerous screws are driven into the bone to facilitate the original setting. Additionally, the devices are often cumbersome and take a relatively long time to set the bone. Because a substantial amount of the tissue around the bone fracture must be opened to provide sufficient access to the bone for pin placement, the patient will usually be given a general anesthetic. By reducing the amount of time necessary to reduce the fracture, the amount of time which the patient must be anaesthetized can be decreased.

Thus, there is a need for a apparatus for externally reducing compound fractures, while simultaneously providing medical personnel with the ability to control torque in the apparatus. Such control would decrease the time necessary to reduce the fracture and prevent injury to the patient and others during the procedure.

SUMMARY OF THE INVENTION

It is an object of the present invention to provide an apparatus which facilitates the proper reduction of compound fractures without the need for placing screws into the misaligned portions of the fractured bone.

It is another object of the present invention to provide a simple and efficient bone reduction apparatus which noninvasively assists in the setting of compound fractures.

It is yet another object of the present invention to provide such a apparatus which is economical and easy to use.

It is still another object of the present invention to provide such an apparatus in which the user can control torque as the apparatus is used to force the fractured bone portions back into alignment, so as to facilitate proper alignment without the risk that the apparatus will slip off of the patient's limb.

It is yet still another object of the present invention to provide such an apparatus which can be used on a variety of bone sizes to facilitate reduction of compound fractures in different limbs and on different portions thereof.

The above and other objects of the invention are realized in specific illustrated embodiments of a bone setting apparatus including an elongate shaft with a proximal end and a distal end. A first working arm is attached to the elongate shaft adjacent the distal end, and a second working arm is attached to the shaft at an intermediate portion between the proximal and distal ends. The first and second working arms are positioned so as to extend generally perpendicular to the shaft. Disposed at the proximal end of the shaft is a torque control mechanism which extends outwardly from the shaft and can be used to control rotation of the shaft about its longitudinal axis as it is pivoted about an axis perpendicular to the shaft and bone in such a manner as to align fractured portions of a bone.

In accordance with one aspect of the present invention the torque control mechanism comprises a T-shaped handle disposed at the proximal end of the elongate shaft. The T-shaped handle is sufficiently wide to be supported by the hand or arm of medical personnel using the apparatus. By controlling the manner in which he or she grips the handle, the physician preforming the procedure can adequately control the torque on the shaft of the apparatus and on the bone to achieve the desired reduction without risk that the apparatus will slip off of the patient's limb.

In accordance with another aspect of the present invention, at least one of the two arms used to reduce the compound fracture has a concave face disposed for contacting the limb having the compound fracture. The concave face contacts a greater area of the effected limb and better conforms to the shape of the limb, thereby reducing the likelihood of accidental slippage during the procedure.

In accordance with still another aspect of the present invention, a pair of generally parallel shafts are provided with the arms extending therebetween. The parallel shafts significantly reduce the amount of torque produced as the bones are forced back into the desired position because the force used to set the bone is applied at both ends of the arms. A handle extending between the two shafts can be used to apply torque to the bone when such is necessary for proper setting.

In accordance with yet another aspect of the present invention, the elongate shaft has and angled portion adjacent the proximal end thereof to prevent the torque control mechanism from interfering with placement of the bone.

In accordance with yet another aspect of the present invention, the bone setting apparatus is readily compactible when not in use.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
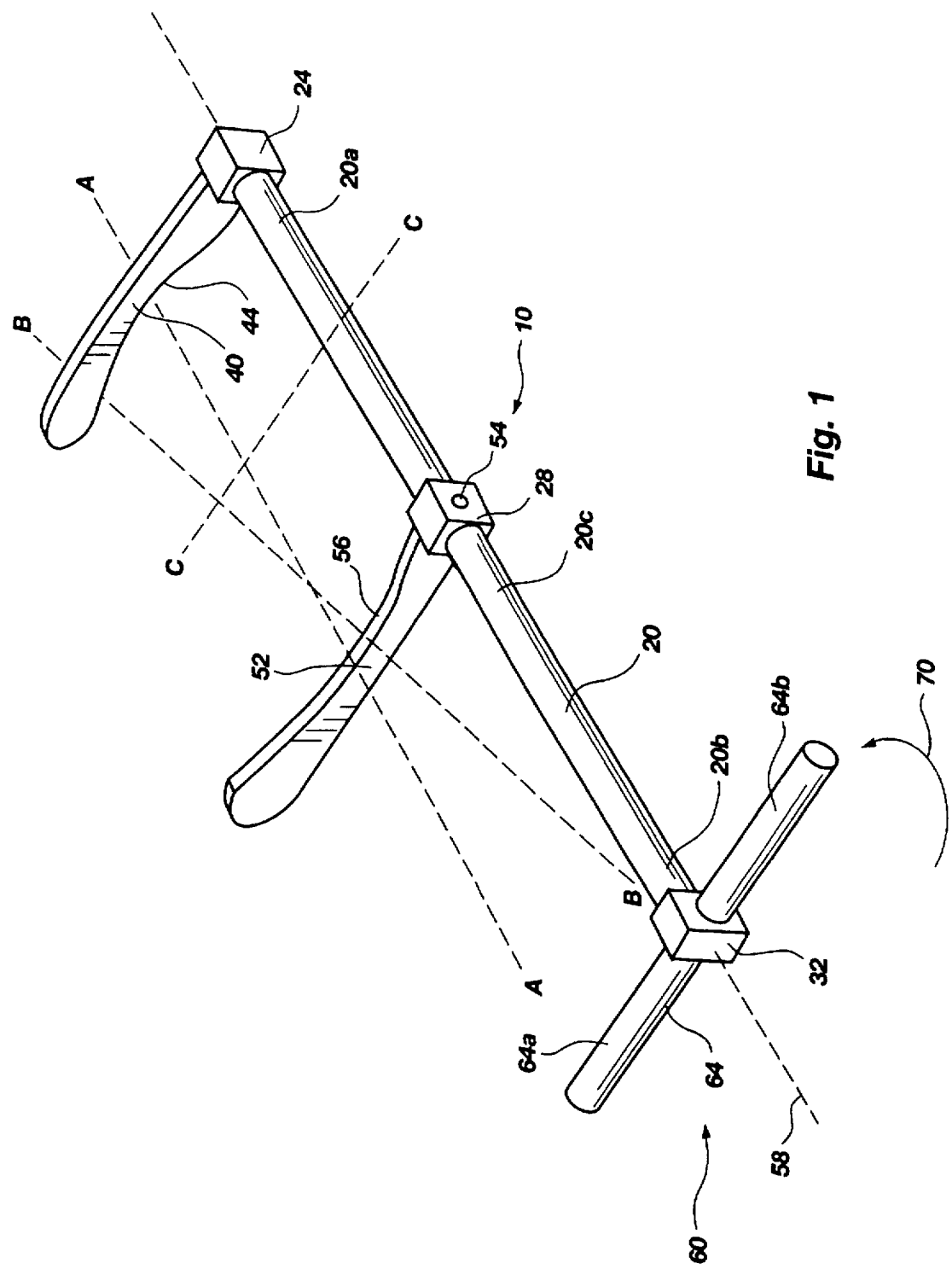
FIG. 1 shows a perspective view of a bone setting apparatus made in accordance with the teachings of the present invention.

Reference will now be made to the drawings in which the various elements of the present invention will be given numeral designations and in which the invention will be discussed so as to enable one skilled in the art to make and use the invention. Referring to FIG. 1, there is shown a perspective view of a bone setting apparatus, generally indicated at 10. The bone setting apparatus 10 includes an elongate shaft 20 having a distal end 20a and a proximal end 20b. Disposed along the elongate shaft 20 are first, second and third connectors, 24, 28, and 32. The first connector 24 is attached adjacent to the distal end 20a of the elongate shaft 10, and may be movable therealong to adjust the bone setting apparatus 10 to the size of the patient.

Attached to the first connector 24 is an elongate first, distal working arm 40 which extends generally perpendicular to the elongate shaft 20. The first working arm 40 has a concave contact surface 44 configured and disposed for interfacing with an injured limb to better hold the limb during setting of the bone. As shown in FIG. 1, the contact surface 44 of the first working arm 40 is disposed on a bottom side thereof for engaging the top of a limb to be set.

Spaced from the first working arm 40 is a second, intermediate working arm 52 which is attached to the shaft 20 by the second connector 28. The second working arm 52 is selectively slidable relative to the shaft 20 along a middle portion 20c of the shaft 20 via movement of the second connector 28. Typically the elongate shaft 20 will be about 36 inches long, and the second connector 28 will have a sliding range of motion of approximately 12 inches. A nut 54 or other fastener is used to secure the second working arm 52 once placed in the desired position.

As with the first working arm 40, the second working arm 52 has a concave contact surface 56 formed therein. The concave contact surface 56 is disposed in an opposite side of the second working arm 52 as compared to concave contact surface 44 of the first arm 40. Thus, when the concave contact surface 44 is disposed above a limb, the elongate shaft 20 will be positioned so that the second working arm 52 is disposed below the limb. Those skilled in the art will appreciate that the concave contact surfaces 44 and 56 can be reversed by simply rotating the elongate shaft 90 degrees about its longitudinal axis 58.

To set a compound fracture, the bone is disposed generally parallel to the elongate shaft along a working axis as indicated by the line A—A. Preferably, the fracture is centered between the first arm 40 and the second arm 52. The elongate shaft 20 is then rotated about an axis perpendicular to the elongate shaft and the working axis, indicated at C—C. Typically, the perpendicular axis C—C about which the shaft 20 is rotated is in alignment with fracture. By applying upward pressure to the proximal end 20b of the elongate shaft 20, the first arm 40 applies a downward force on the bone, and the second arm 44 applies an upward force on the bone. The opposing forces of the first and second arms 40 and 44 force the bone into alignment.

Unlike the prior art, however, the concave nature of the first and second working arms 40 and 52 significantly decrease the risk of slipping as the proximal end 20b of the elongate shaft 20 is lifted upwardly. Because the curvatures of contact surfaces 44 and 56 engage a larger amount of the surface area of the limb and prevent a sudden linear movement, the risk of torque causing the bone setting apparatus to move is reduced.

To further increase stability, the two contact surfaces 44 and 56 are disposed in general alignment along the working axis A—A, which is generally parallel with the longitudinal axis 58 of the shaft. In use, the bone portions to be reduced typically will be disposed so that the bone extends along the working axis. However, because the pressure is supplied from one lateral side of the working axis, there is a tendency for the bone setting apparatus to apply force along an axis tangential to the working axis A—A. Thus, for example, applying an upward force to the proximal end 20b to rotate the elongate shaft 20 about axis C—C can produce an actual working axis along the line indicated at B—B unless torque on the elongate shaft is controlled. This can cause improper alignment of the bone, and can, in extreme cases, cause sufficient torque in the bone setting apparatus 10 that the apparatus slips from the limb being set. The concave contact surfaces 44 and 56 reduce the risk of slippage due to their improved conformity with the limb. However, they are often insufficient in and of themselves to control the significant amount of torque which is present.

To control the significant torque which may be developed and to assist the physician in working the pieces of bone into alignment, a torque control mechanism, generally indicated at 60 is disposed at the proximal end 20b of the elongate shaft 20. As shown in FIG. 1, the torque control mechanism 60 includes a handle 64 formed by first and second bars 64a and 64b which extend generally perpendicular to the elongate shaft 20. The first and second bars 64a and 64b are attached to the elongate shaft 20 by the third connector 32.

The bars 64a and 64b are very useful in controlling torque and misalignment in the bone setting apparatus 10 during use. When used as shown in FIG. 1, i.e. the first working arm 40 being disposed above the limb and the second working arm 52 being disposed below the limb, the bone setting apparatus 10 will tend to apply force along the actual working axis B—B and develop torque in the elongate shaft in a counter-clockwise orientation, as indicated by arrow 70. To prevent the misalignment and torque so developed from interfering with the setting of bones, the upward force applied to the second end 20b of the elongate shaft will typically be done via the first bar 64a of the handle 64. The upward force on the first bar 64a creates a counter-torque of a similar magnitude with that indicated at 70, and causes the actual working axis to be more in line with the working axis A—A along which the bone is typically disposed. This is most easily accomplished by placing the hand lifting the proximal end 20b along the first bar 64a as close as possible to the working axis A—A. In such a manner, the torque created by the working arms 40 and 52 and the handle 64 effectively cancel each other out and the risk that the bone setting apparatus 10 will slip is greatly decreased. When combined with the concave contact surfaces of the working arms 40 and 52, the occurrence of slippage can be virtually eliminated.

In the event that additional torque is present (or necessary) due to the angle at which the fracture must be reduced, additional counter-torque can be provided by placing a small amount of force on the second bar 64b of the handle in a direction opposite the direction which the proximal end 20a is being moved. If the proximal end 20b of the shaft 20 is being lifted, a small downward force on the second bar 64b will significantly reduce torque. Of course, the further from the elongate shaft 20 the downward force is applied, the less downward force which must be used while effectively off-setting the torque/misalignment created by forcefully lifting the proximal end 20b of the elongate shaft 20. Thus, both the first and second handles 64a and 64b serve as moment arms which extend generally perpendicularly from the shaft 20 to increase control. If desired, the orientation of the bars 64a and 64b could be disposed in some arrangement other than perpendicular to the elongate shaft 20.

In addition to using the handle 64 to off-set torque, the physician can also use the handle to align the bone portions being set. When reducing the fracture, it will often be found that the bones are not in perfect alignment along the planned working axis A—A. This is why many of the currently used devices utilize an invasive network of screws which allow three dimensional adjustment of the bones. By moving the point at which his or her hand applies pressure to the bars 64a and 64b of the handle 64, the physician can use the handle 64 of the present invention to adjust the actual working axis as the shaft 20 is being rotated about the perpendicular axis C—C until the fracture is properly reduced. Thus, the handle 64 not only controls unwanted torque along the shaft, it can also be used to apply toque to bone to achieve improved reduction.

As shown in FIG. 1, the shaft 20 is generally linear. However, in some applications a linear shaft would result in interference between the handle 64 and a limb placed along the working axis A—A. To overcome such situations, the shaft 20 could be bent adjacent the proximal end 20b or at some other an appropriate location so that the handle 64 is not in direct alignment or in the same plane with the first and second working arms 40 and 52. Such an arrangement is present in the shafts shown in FIGS. 2 and 3. Some physicians will find that different angles will facilitate use in the reduction of fractures in various orientations. Thus, several different angles may be provided to customize the bone setting apparatus 10 to the desires of the physician.

Figure 2:
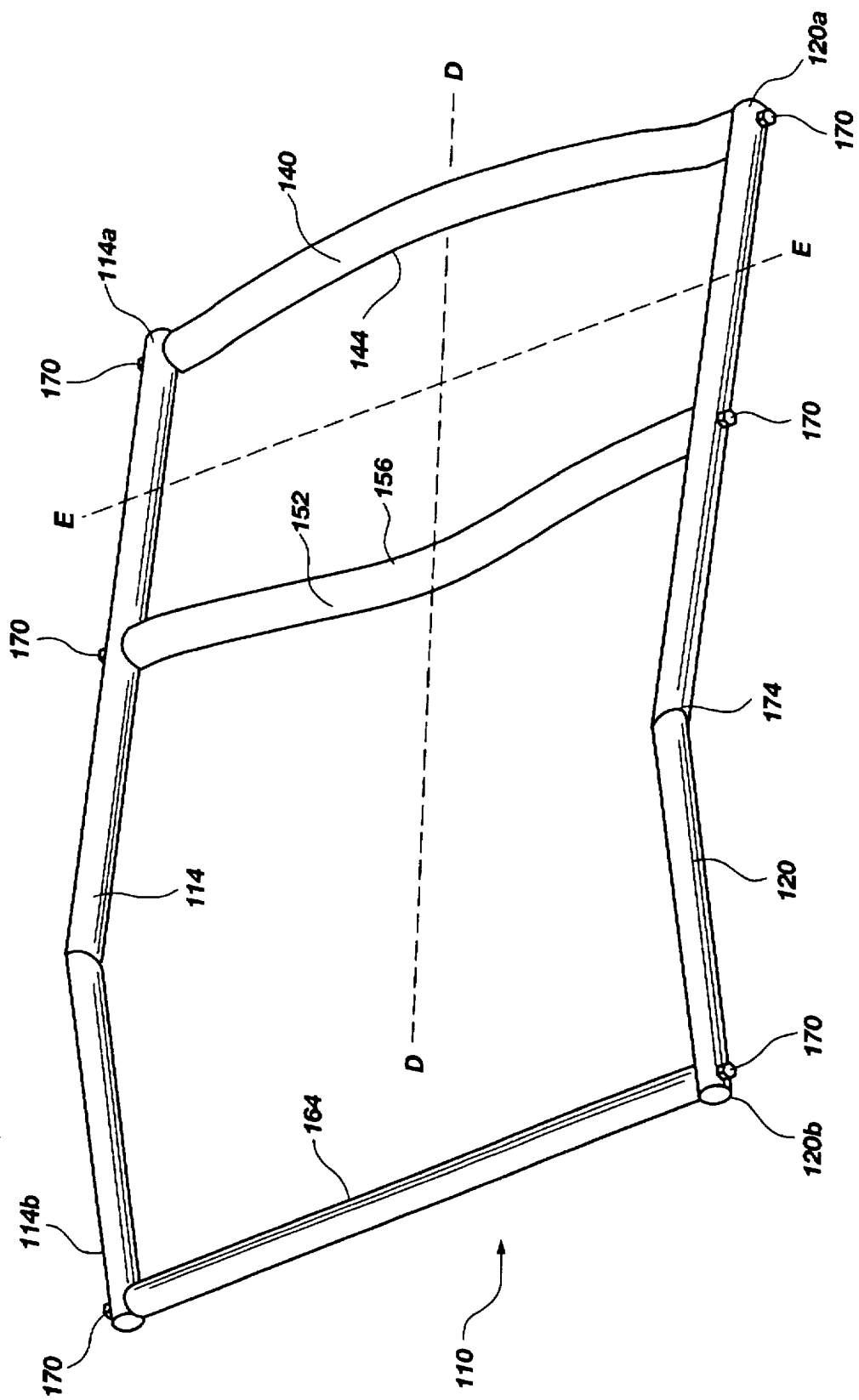
FIG. 2 shows a perspective view of an alternate embodiment of the present invention.

Referring now to FIG. 2, there is shown an alternate embodiment of the present invention. The bone setting apparatus, generally indicated at 110, includes a first elongate shaft 114 and a second elongate shaft 120. Each of the shafts 114 and 120 are angled to facilitate ease of use next to a limb having a fracture which must be reduced. The angle prevents the handle (discussed below) and limb being set from interfering with one another.

Extending between the first and second elongate shafts 114 and 120 are first and second working arms 140 and 152, respectively. The first working arm 140 is disposed at distal ends 114a and 120a of the first and second elongate shafts 114 and 120. The first working arm 140 is generally cylindrical, but is molded or bent to provide a generally concave contact surface 144 in a middle portion thereof. As shown in FIG. 2, the first working arm 140 does not move with respect to the first and second elongate shafts 114 and 120.

A second working arm 152 is disposed in a middle portion of the apparatus between the distal and proximal ends 114a, 120a, 114b and 120b of the first and second elongate shafts 114 and is positioned so as to extend generally parallel to the first working arm 140. As shown in FIG. 2, the first and second work arms 140 and 152 are not completely parallel because of a concave contact surface 156 of the second working arm extends in an opposite direction from the concave contact surface 144 of the first working arm 140. This allows the first and second working arms 140 and 152 to be positioned on opposing sides of a limb and for the limb to nest into the concave contact surfaces of the arms. Typically, the concave contact surfaces 144 and 156 will be in alignment along a central axis D—D of the bone setting apparatus 10.

Figure 3:
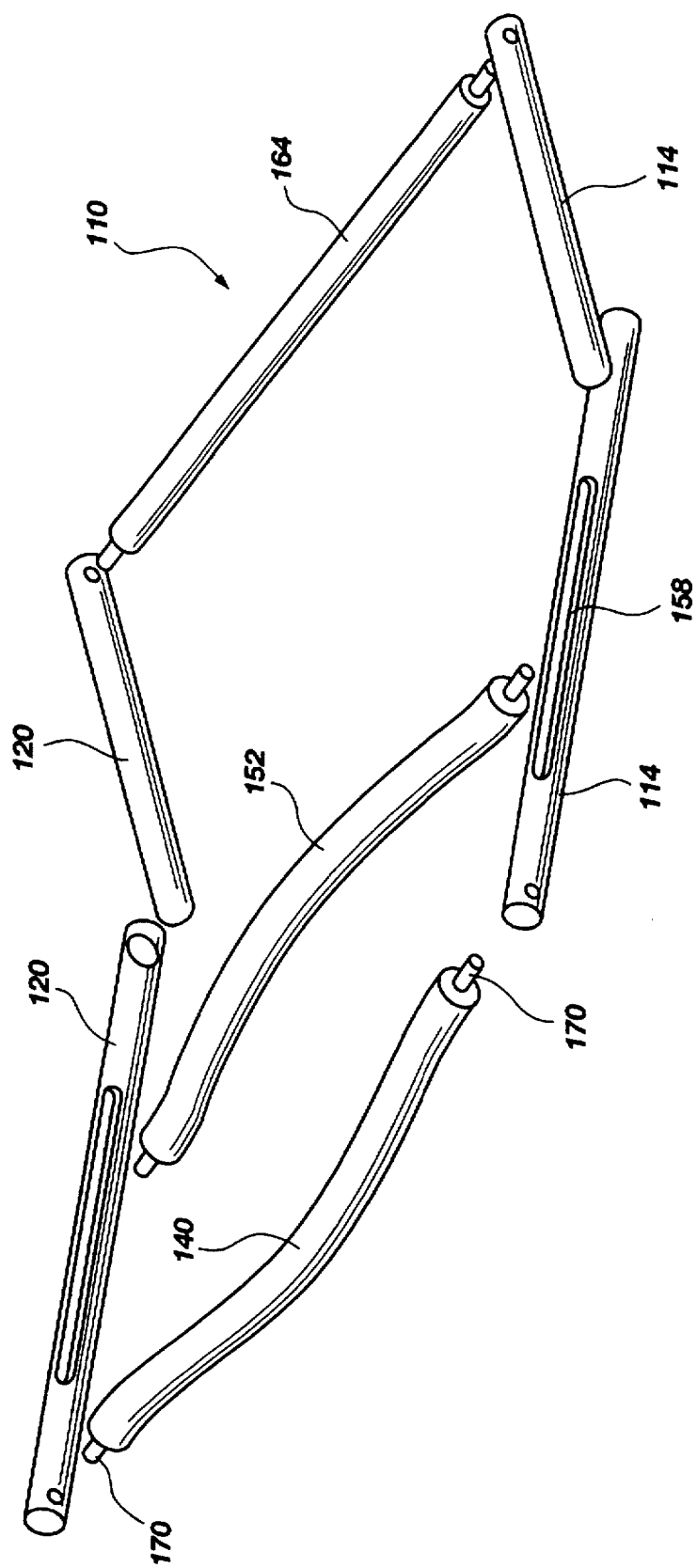
FIG. 3 shows an exploded view of the alternate embodiment of the present invention.

As is shown more clearly in FIG. 3, the second working arm 152 is attachable so as to slide along a track 158 in shafts 114 and 120 when desired. The track 158 enables the second working arm 152 to be moved as close as 12 inches to the first working arm 140, or as far away as 24 inches therefrom. This enables the medical personnel to provide the appropriate positioning of the work arms 140 and 152, as well as to control the amount of leverage which is provided by the elongate shafts 114 and 120.

Also disposed between the shafts 114 and 120 is a generally linear handle 164 formed by an elongate bar. The handle 164 enables both of the elongate shafts 114 and 120 to be pivoted in the same direction about a perpendicular axis E—E, thereby applying torque to a limb disposed along the working axis D—D, without generating a rotational torque about the longitudinal axis of either elongate shaft 114 or 120. As with the embodiment discussed in FIG. 1, it is usually preferable to align the perpendicular axis E—E with the fracture.

If the working arms 140 and 152 must be used at an angle in which they are not generally perpendicular to the limb, the elongate handle 164 enables the user to easily counteract any torque developed. This can be accomplished by simply moving the hand applying upward (or other directional) pressure on the handle 164 to a position in which balance is achieved. In the alternative, the handle 164 can be used to apply a small amount of torque to the limb disposed between the first and second working arms 140 and 152 to ensure that the two pieces of bone are in proper alignment. By either rotating the handle relative to the central axis D—D, or by pushing the handle 164 to either side, the physician is given improved three dimensional control of the bone. The extent of movement will depend on the misalignment of the bones and can be readily determined by the physician.

Referring now specifically to FIG. 3, there is shown a disassembled view of the embodiment shown in FIG. 2. Because storage space is often limited in hospitals due to the large number of medications and apparatuses which must be present, the embodiment shown in FIG. 2 can quickly and easily be disassembled. Bolts 170 are used to hold the first and second working arms 140 and 152, and the handle 164. By removing the bolts, the working arms 140 and 152 and the handle 164 can be removed from the elongate shafts 114 and 120, thereby allowing the bone setting apparatus 110 to be compacted. Furthermore, as shown in FIG. 2, each elongate shaft is formed from two elongate tubes. A bolt 174 is used to connect the two pieces and removal of the bolt allows further compacting of the elongate shafts 114 and 120 of the bone setting apparatus 110. With bolt 174 removed, the longest piece of the disassembled bone setting apparatus 110 is 24 inches or less.

If desired, the bolts 174 can also be used to adjust the relative positions of the elongate tubes which form each shaft 114 and 120. By controlling the relative positions of the elongate tubes, the position of the handle 164 can be adjusted to that desired by the physician.

Thus, there is disclosed an improved bone setting apparatus. Those skilled in the art will recognize numerous modifications which can be made without departing from the scope and spirit of the invention. The appended claims are intended to cover such modifications.

What is claimed is:

1. An apparatus for facilitating the reduction of compound fractures within a limb, the apparatus comprising:

a first rigid elongate shaft having a proximal end and a distal end;

a distal working arm and an intermediate working arm connected to said shaft and extending generally perpendicularly thereto, said arms being generally parallel to each other with each being configured for engaging a portion of a limb on opposing sides of the fracture and for applying torque about an axis generally perpendicular to said elongate shaft and between said working arms when said elongate shaft is pivoted relative to the limb, each of said arms having a concave portion for engaging the limb, the concave portion of the distal working arm being disposed on an opposite side as the concave portion of the intermediate working arm to facilitate engagement of opposing sides of the limb; and torque control means connected at the proximal end of the elongate shaft and spaced from the working arms for controlling the rotation of the elongate shaft about its longitudinal axis when the elongate shaft is pivoted with respect to said limb to apply torque to said limb about said perpendicular axis, said torque control means comprising a bar extending outwardly and generally perpendicular to said elongate shaft.

2. The apparatus of claim 1, wherein the torque control means comprises a handle having a bar extending perpendicularly from the elongate shaft generally in parallel with the distal and intermediate working arms.

3. The apparatus of claim 1, wherein the concave portion of the distal working arm comprises a generally concave contact surface configured for engaging a limb when the elongate shaft is pivoted with respect to the limb.

4. The apparatus of claim 3, wherein the distal and intermediate working arms each comprise a generally concave contact surface configured for engaging a limb when the elongate shaft is pivoted about the perpendicular axis.

5. The apparatus of claim 4, wherein the distal and intermediate working arms each have an upper side and a lower side, and wherein the concave contact surface of the distal working arm is disposed in the lower side of the distal working arm and wherein the concave contact surface of the intermediate working arm is disposed in the upper side thereof.

6. The apparatus of claim 1, wherein the distal and intermediate working arms each include a concave contact surface formed therein for engaging the limb when the elongate shaft is pivoted about the perpendicular axis.

7. The apparatus of claim 1, wherein the apparatus further comprises a second elongate shaft attached to the distal and intermediate working arms and disposed in parallel to the first elongate shaft.

8. The apparatus of claim 7, wherein the torque control means comprises a handle extending between the first and second elongate shafts.

9. An apparatus for facilitating the reduction of compound fractures within a limb, the apparatus comprising:

a first rigid elongate shaft having a proximal end and a distal end;

a distal working arm and an intermediate working arm connected to said shaft and extending generally perpendicularly thereto, said arms being generally parallel to each other with each being configured for engaging a portion of a limb on opposing sides of the fracture and for applying torque about an axis generally perpendicular to said elongate shaft and between said working arms when said elongate shaft is pivoted relative to the limb; and torque control means connected at the proximal end of the elongate shaft and spaced from the working arms for controlling the rotation of the elongate shaft about its longitudinal axis when the elongate shaft is pivoted with respect to said limb to apply torque to said limb about said perpendicular axis, the torque means comprising a handle having a bar extending generally perpendicular from the elongate shaft on a side opposite laterally the distal and intermediate working arms.

10. An apparatus for facilitating the reduction of compound fractures within a limb, the apparatus comprising:

a first rigid elongate shaft having a proximal end and a distal end;

a distal working arm and an intermediate working arm connected to said shaft and extending generally perpendicularly thereto, said arms being generally parallel to each other with each being configured for engaging a portion of a limb on opposing sides of the fracture and for applying torque about an axis generally perpendicular to said elongate shaft and between said working arms when said elongate shaft is pivoted relative to the limb; and torque control means connected at the proximal end of the elongate shaft and spaced from the working arms for controlling the rotation of the elongate shaft about its longitudinal axis when the elongate shaft is pivoted with respect to said limb to apply torque to said limb about said perpendicular axis, said torque control means comprising a handle having a bar extending perpendicularly from the elongate shaft generally in parallel with the distal and intermediate working arms, and wherein the elongate shaft is angled so that the bar of the handle is disposed out of alignment with the distal and intermediate working arms.

11. An apparatus for reducing compound fractures in a limb, the apparatus comprising:

a first elongate shaft having a longitudinal axis having a proximal end and a distal end;

a distal working arm extending generally perpendicularly from the first elongate shaft adjacent the distal end thereof, the distal working arm having a concave contact surface disposed therein for engaging a limb;

an intermediate working arm extending generally perpendicularly from the first elongate shaft and spaced from the distal working arm, the intermediate working arm having a concave contact surface disposed therein for engaging a limb, the concave contact surface of the intermediate working arm being disposed opposite the concave contact surface of the distal working arm so as to facilitate placement of the working arms on opposing sides of a limb; and handle means attached to the proximal end of the first elongate shaft for controlling rotation of the first elongate shaft about the longitudinal axis thereof, the handle means comprising at least one elongate bar extending perpendicularly from the first elongate shaft.

12. The apparatus of claim 11, wherein the distal working arm has an upper side and a bottom side, and wherein the bottom side forms the concave contact surface.

13. The apparatus of claim 11, wherein the intermediate working arm has an upper side and a bottom side, and wherein the upper side forms the concave contact surface.

14. The apparatus of claim 11, wherein the apparatus further comprises a second elongate shaft attached to the distal and intermediate working arms on a side opposite the first elongate shaft, the second elongate shaft and the first elongate shaft being disposed in parallel.

15. The apparatus of claim 14, wherein the handle means extends from the first elongate shaft to the second elongate shaft.

16. The apparatus of claim 11, wherein the handle means comprises a first bar extending perpendicularly from the first elongate shaft and a second bar disposed coaxially with the first bar and extending outwardly from the elongate shaft on a side opposite the first bar.

17. A method for reducing a compound fracture in a limb, the method comprising:

a) selecting a bone setting apparatus having an elongate shaft having a longitudinal axis and proximal and distal ends with a distal working arm extending generally perpendicular to the elongate shaft, the distal working arm being disposed adjacent the distal end of the elongate shaft, an intermediate working arm spaced proximally from the distal working arm and disposed generally parallel to the distal working arm, each arm having a concave contact surface, and a handle mechanism extending from the proximal end of the elongate shaft for controlling rotation of the elongate shaft about its longitudinal axis;

b) disposing the distal working arm adjacent the limb so that the limb contacts the distal working arm along the concave contact surface of the distal working arm;

c) disposing the intermediate working arm adjacent the limb so that the limb contacts the intermediate working arm along the concave contact surface of the intermediate working arm and so that the fracture is disposed between the distal and intermediate working arms;

d) pivoting the elongate shaft so that the one of the working arms presses downwardly on the limb and the other working arm presses upwardly on the limb; and e) applying pressure to the handle mechanism to control rotation of the elongate shaft about its longitudinal axis.

18. The method of claim 17, wherein step (a) comprises, selecting a bone setting apparatus having a second elongate shaft attached to the distal and intermediate working arms and disposed in parallel with the first elongate shaft.

19. The method of claim 18, wherein step (a) comprises, more specifically, selecting a bone setting apparatus having a handle mechanism in the form of a bar extending between the first and second shafts.

20. The method of claim 17, wherein step (d) comprises, more specifically, lifting upwardly on the handle mechanism.

21. An apparatus for facilitating the reduction of compound fractures within a limb, the apparatus comprising:

a first rigid elongate shaft having a proximal end and a distal end; and a distal working arm and an intermediate working arm connected to said shaft and extending generally perpendicularly thereto, said arms being generally parallel to each other with each being configured for engaging a portion of a limb on opposing sides of the fracture and for applying torque about an axis generally perpendicular to said elongate shaft and between said working arms when said elongate shaft is pivoted relative to the limb, each of said arms having a concave portion for engaging the limb, the concave portion of the distal working arm being disposed on an opposite side as the concave portion of the intermediate working arm to facilitate engagement of opposing sides of the limb.

* * * * *